United States Patent [19]
White et al.

[11] Patent Number: 5,821,185
[45] Date of Patent: Oct. 13, 1998

[54] SOLID STATE PROTON AND ELECTRON MEDIATING MEMBRANE AND USE IN CATALYTIC MEMBRANE REACTORS

[75] Inventors: James H. White; Michael Schwartz; Anthony F. Sammells, all of Boulder, Colo.

[73] Assignee: Eltron Research, Inc., Boulder, Colo.

[21] Appl. No.: 492,949

[22] Filed: Jun. 21, 1995

Related U.S. Application Data

[62] Division of Ser. No. 182,977, Jan. 14, 1994, abandoned.

[51] Int. Cl.$^6$ .............................. B01J 21/10; B01J 23/34; B01J 35/00
[52] U.S. Cl. .............................. 502/4; 502/302; 502/303; 502/304; 502/305; 502/306; 502/308; 502/309; 502/311; 502/325; 502/326; 502/328
[58] Field of Search .................................... 502/302, 303, 502/304, 305, 306, 308, 309, 311, 325, 326, 328, 4

[56] References Cited

U.S. PATENT DOCUMENTS

| | | | |
|---|---|---|---|
| 3,350,846 | 11/1967 | Makrides et al. ............................ | 95/56 |
| 3,361,834 | 1/1968 | Lester ...................................... | 585/403 |
| 3,375,288 | 3/1968 | Russet ...................................... | 585/403 |
| 3,393,098 | 7/1968 | Hartner et al. ............................. | 429/13 |
| 4,388,479 | 6/1983 | Gryaznov et al. ......................... | 568/828 |
| 4,468,235 | 8/1984 | Hill ............................................. | 55/16 |
| 5,139,541 | 8/1992 | Edlund et al. ............................. | 55/16 |
| 5,210,059 | 5/1993 | Matturo et al. ............................. | 502/4 |
| 5,217,506 | 6/1993 | Edlund et al. ............................. | 55/16 |
| 5,266,204 | 11/1993 | Clough et al. ............................ | 502/4 |

OTHER PUBLICATIONS

Hibino, T. et al. (1992, "Electrochemical Methane Activation to $C_2$–Hydrocarbons Using Protonic Conductor," *Chem. Lett.*, pp. 1715–1716.

Chiang, P–H. et al. (1991), "Electrocatalytic Methane Dimerization with a Yb–Doped $SrCeO_3$ Solid Electrolyte," *J. Electrochem. Soc.* 138(6):L11–L12.

Weaver, D. and Winnick, J. (1991), "Evaluation of Cathode Materials for the Electrochemical Membrane $H_2S$ Separator," *J. Electrochem. Soc.* 138(6):1626–1636.

Bonanos, N et al. (1991), "Construction and operation of fuel cells based on the solid electrolyte $BaCeO_3$:Gd," *Solid State Ionics* 44:305–311.

Bonanos, N. et al. (1988), "Oxide Ion Conduction in Ytterbium–Doped Strontium Cerate," *Solid State Ionics* 28–30:579–584.

White, J.H. et al. (1992), "The electrochemical oxidative dimerization of methane," *Solid State Ionics* 53–56:149–161.

*Primary Examiner*—Elizabeth D. Wood
*Attorney, Agent, or Firm*—Greenlee, Winner & Sullivan, P.C.

[57] ABSTRACT

This invention provides catalytic proton and electron mediating membranes useful in catalytic reactors. The membranes have an oxidation and a reduction surface and comprise a single-phase mixed metal oxide material of the formula:

$$AB_{1-x}B'_xO_{3-y}$$

wherein A is selected from Ca, Sr or Ba ions; B is selected from Ce, Tb, Pr, or Th ions; B' is selected from Ti, V, Cr, Mn, Fe, Co, Ni, Cu, Al, Ga, or In ions, or combinations thereof; and x is greater than or equal to 0.02 and less than or equal to 0.5. The membranes can further comprise a catalyst on either the oxidation or reduction surface, or both. Membranes include those which are fabricated-by combining powders of metal oxides or metal carbonates of metal A ion, metal B ion and metal B' ion such that the stoichiometric ratio A:B:B' is 1:1-x:x where $0.2 \leq x 0.5$, repeatedly calcining and milling the combined powders until a single-phase material is obtained and pressing and sintering the single-phase material to obtain a membrane.

23 Claims, 6 Drawing Sheets

SOLID STATE PROTON AND ELECTRON MEDIATING MEMBRANE AND USE IN CATALYTIC MEMBRANE REACTORS

This application is a division of U.S. Ser. No. 08/182,977, filed on Jan. 14, 1994 and now abandoned.

This invention was made with government support under Contract No. DE-FG0290ER81165, awarded by the Department of Energy and under Contract No. 111-9260336 awarded by the National Science Foundation. The United States Government has certain rights in this invention.

TECHNICAL FIELD

This invention relates to solid state materials fabricated into membranes for use in catalytic reactors, and more particularly to membranes for use in catalytic membrane reactors for promoting dehydrogenation of hydrocarbons or alcohols, oligomerization of hydrocarbons including methane, and for the decomposition of hydrogen-containing gases. The invention also includes the use of catalysts to facilitate the above reactions. Solid state materials for membrane use include materials crystallizing in the perovskite structure which are known to be proton and electron conductors. Examples of catalytic membrane reactions include the oligomerization of methane to yield ethane, dehydrogenation of ethane to yield ethylene, the decomposition of $H_2S$ to yield S and $H_2O$ or $H_2$, and $H_2$ separation.

BACKGROUND ART

Catalytic membrane reactors using solid state membranes for facilitating various chemical reactions have been studied and used previously. For the membranes of the present invention, a valuable use of such catalytic reactors is in the oligomerization of methane to produce ethylene as a means to replace existing ethylene synthesis technology.

Currently in the U.S., approximately 75% of feedstock for ethylene production comes from natural gas liquids, primarily ethane and propane. The remaining 25% is obtained using naphtha derived from petroleum processing. Conventional technology is to "thermally crack," i.e. heat, the feedstock to produce ethylene. This produces ethylene, along with secondary reaction products. The cost of separating ethylene from the secondary reaction products can amount to 50% of the total process cost.

By contrast, catalytic reaction to achieve the same end result may utilize natural gas as the feedstock. Because of its very simple molecular structure, the use of natural gas as the feedstock minimizes the formation of secondary reaction products, thereby providing a clear cost advantage. However, current production of ethylene from natural gas using conventional catalytic reactors has a production efficiency of about 25%, whereas 40% efficiency is needed to achieve-economic viability. In contrast to this, catalytic membrane reactors can achieve efficiencies close to 100%, with selectivity to ethylene also close to 100%.

All materials to be used in membrane reactors for the above-cited reactions must meet three requirements. First, they must be conductors of protons. The reactions of interest in this invention are based on the loss of hydrogen from the hydrogen-containing gas and therefore the membrane must be capable of mediating hydrogen away from the reaction surface. This hydrogen is converted into protons at the membrane surface and it is in the form of protons that the hydrogen is transferred through the membrane from the zone containing the hydrogen-containing gas to the zone with the oxygen-containing gas or vacuum.

The second requirement for the membrane is the ability to conduct electrons. The reactions involving the loss of hydrogen from the hydrogen-containing gas, the transformation of this hydrogen into protons, and the subsequent recombination or reaction of these protons with the oxygen-containing gas are electrochemical and therefore generate or consume electrons. To maintain electrical balance, the electrons generated on the oxidizing surface of the membrane must migrate to the reducing surface on the other side of the membrane where they are consumed. Therefore, the membrane must be electrically conducting in order to allow for the transfer of electrons.

Finally, the third requirement for any materials to be used in membrane reactors is chemical and mechanical stability at the temperatures of operation and under the conditions of operation. Any reaction of the membrane material with the reactant gases leading to decomposition will cause the membrane to simply deteriorate with loss of proton and/or electron conductivity or failure of the membrane to completely separate the two reactant zones leading to direct reaction between the hydrogen-containing and oxygen-containing gases.

Perovskite materials have previously been used as membranes to facilitate the oligomerization of methane to ethylene (T. Hibino, S. Hamakawa and H. Iwahara, Chem. Lett., 1715 (1992) and P. H. Chiang, D. Eng and M. Stoukides, J. Electrochem Soc., 138, 611 (1991). Hibino and Chiang used the proton conductor $SrCe_{0.95}Yb_{0.05}O_{3-x}$ as the membrane material. Although this material is a proton conductor, it is not an electrical conductor and therefore does not meet the second requirement listed above. To use this particular material as the membrane in a catalytic membrane reactor, electrical current needs to flow through an external electrical circuit, complicating the reactor design. Also in both cases, product formation was minimal until a current was applied. This requires an energy input and adds expense to the cost of ethylene production. This is in contrast to the present invention in which electron conductivity is an inherent feature of the membrane and products are produced spontaneously, i.e. without added energy.

Two other types of membranes are known to achieve $H_2$ transport. These are metal membranes and microporous membranes. An example of the former type is given in U.S. Pat. Nos. 4,388,479 and 3,393,098. This type of membrane suffers from the disadvantage of the expense associated with the metals which allow $H_2$ diffusion. The microporous type membranes are fragile, difficult to fabricate, not completely selective to $H_2$, and are not electrically conducting.

Among the metal type of membranes for $H_2$ transport, earlier patents (U.S. Pat. Nos. 4,468,235 and 3,350,846) have addressed the problem of the high expense of these membranes by forming the membrane from a less expensive transition metal coated with the expensive $H_2$-transporting metal. However, this approach raises the problem of reaction between the two metals resulting in loss of $H_2$-transporting ability. Edlund et al. in U.S. Pat. Nos. 5,139,541 and 5,217,506 address this problem by interposing an inert proton-conducting material between the two metals. This serves as a buffer between the two metals to prevent reaction while still maintaining the $H_2$-transporting ability. Rather than using such a complex membrane, the current invention eliminates the use of the metal layers and forms the membrane directly from an electron- and proton-conducting oxide. This results in an inexpensive and rugged membrane.

In one of the above-cited applications, the membrane reactor will be used to decompose $H_2S$. For decomposition of $H_2S$, a membrane reactor has previously been described by D. Weaver and J. Winnick, J. Electrochem Soc., 138, 1626 (1991). In this reactor, the electrolyte serves to transport S anions, not protons. Although useful for this specific reaction, it clearly is not applicable to hydrocarbon dehydrogenation or oligomerization reactions.

DISCLOSURE OF THE INVENTION

In accordance with this invention a solid state catalytic membrane for reacting a hydrogen-containing gas with an oxygen-containing gas, an inert gas or a partial vacuum in an oxidation-reduction reaction is provided. The membrane is made from mixed electron-and proton-conducting materials fabricated from perovskite compounds. The membrane includes a reduction surface of said membrane exposed to the oxygen-containing gas of said reaction and an oxidation surface of said membrane exposed to the hydrogen-containing gas of said reaction. Preferably, the single-component mixed electron- and proton-conducting materials are fabricated from perovskite compounds having general stoichiometry $AB_{1-x}B'_xO_{3-y}$, wherein: the A elements are taken from the group consisting of Ca, Sr or Ba; the B elements are taken from the group consisting of Ce, Tb, Pr or Th; the B' elements are taken from the group consisting of Ti, V, Cr, Mn, Fe, Co, Ni, Cu, Al, Ga or In, or combinations thereof; and x is greater than or equal to 0.02 and less than or equal to 0.5. The efficiency of the membrane may be significantly increased by the use of catalysts on the oxidation surface and/or the reduction surface. The specific catalysts vary according to the particular reaction to be catalyzed. Appropriate catalysts for various reactions are discussed in detail below.

Additionally, a catalytic membrane reactor for reacting a hydrogen-containing gas with an oxygen-containing gas, an inert gas or a partial vacuum in an oxidation-reduction reaction may be constructed using the above-described membrane. The reactor comprises at least one reactor cell having a reduction zone and an oxidation zone separated by a membrane of the present invention, and having an entrance port, an exit port, and a passage therebetween for the movement of one or more gases from the entrance port to the exit port.

A process for oligomerizing a hydrogen-containing gas may also be performed with the membrane reactor of the present invention. The process comprises the steps of:

(A) providing at least one catalytic membrane reactor cell having an oxidation zone and a reduction zone separated by a mixed electron- and proton-conducting membrane fabricated from a single-component mixed metal oxide;

(B) heating the catalytic membrane cell to a temperature from 300° C. to 1200° C.;

(C) passing an oxygen-containing gas, inert gas or partial vacuum in contact with the membrane in the reduction zone; and (D) passing a gas capable of being oligomerized through loss of hydrogen in contact with the membrane in the oxidation zone.

Based on the foregoing, several advantages of the present invention are readily apparent. In contrast with current production of ethylene from natural gas using conventional catalytic reactors which have a production efficiency of about 25%, a catalytic membrane reactor is provided which can achieve efficiencies close to 100%, with selectivity to ethylene also close to 100% In addition, the reactor of the present produces products spontaneously, i.e. without added energy. Further, rather than using a complex buffered membrane, the current invention eliminates the use of metal layers and forms the membrane directly from an electron- and proton-conducting oxide. This results in an inexpensive and rugged membrane.

Additional advantages of this invention will become apparent from the description which follows, taken in conjunction with the accompanying drawings.

BEST MODE FOR CARRYING OUT THE INVENTION

Figure 1:
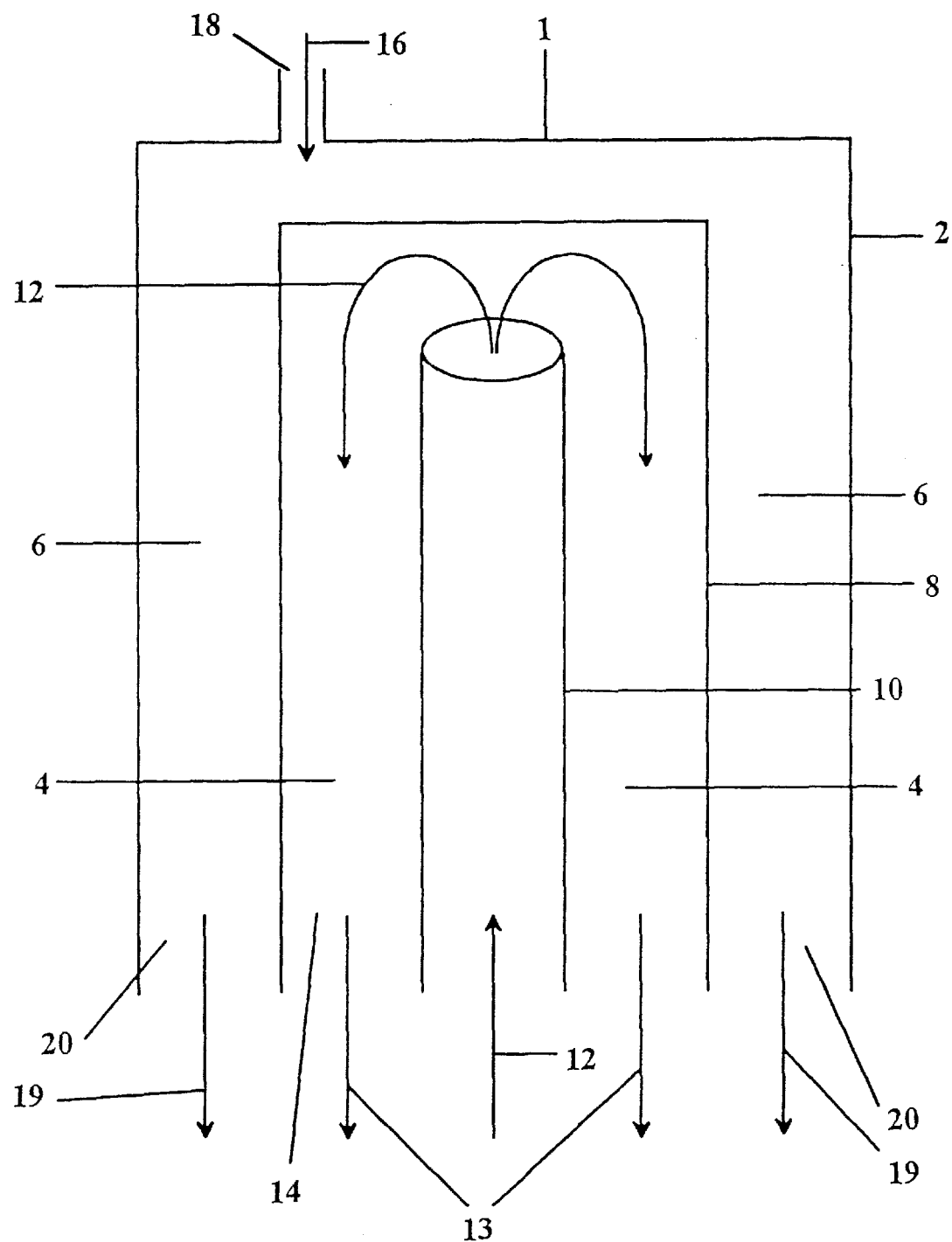
FIG. 1 is a schematic view of a single-cell catalytic reactor embodying the present invention.

Referring now to the drawings, a single-cell catalytic membrane reactor of the present invention may be schematically represented as shown in FIG. 1. The reactor 1 includes a cell 2 having an oxidation zone 4 separated from a reduction zone 6 by a solid state membrane 8. The membrane 8 of the present embodiment is cylindrical in shape, but any shape capable of creating two separate zones would be sufficient. The outer perimeter of the oxidation zone 4 is defined by the membrane 8 and the outer perimeter of the reduction zone 6 is defined by the shell 2. The membrane has a reduction surface 7 facing the reduction zone 6, and an oxidation surface 5 facing the oxidation zone 4. Feed tube 10 delivers a hydrogen-containing gas 12 into the oxidation zone 4. Reacted gases 13 exit the oxidation zone 4 via at least one exit port 14. An oxygen-containing gas 16 is delivered into the reduction zone 6 via entrance port 18. Reacted gases 19 exit the reduction zone 6 via exit port 20. Examples of processes which may be conducted with the present invention are the oligomerization of methane to produce ethylene, dehydrogenation of alkanes to form alkenes, dehydrogenation of alkenes to form alkynes, dehydrogenation of alcohols to form aldehydes or ketones, the decomposition of $H_2S$ to $H_2O$ and S, and the separation of hydrogen from a mixture of gases.

Figure 2:
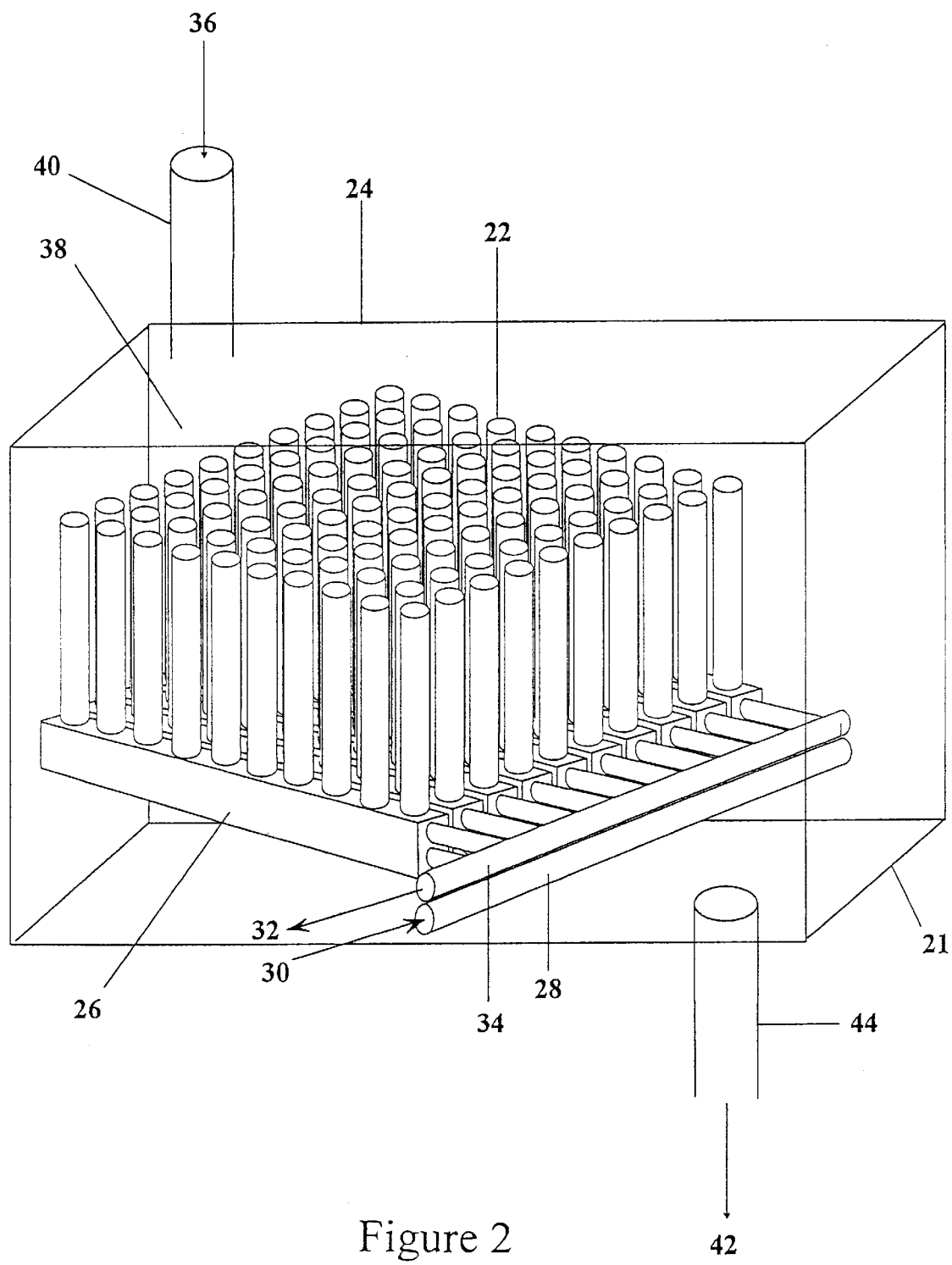
FIG. 2 is a perspective view of a multiple-membrane catalytic reactor.

Referring now to FIG. 2, there is depicted a multiple-cell reactor 21 utilizing cells 22 of the type described above and depicted in FIG. 1. The cells 22 are enclosed in a reactor module 24, and are linked together by manifold 26. An inlet feed tube 28 delivers hydrogen-containing gas 30 to reactor cells 22, and reacted gas 32 exits the cells via the manifold 26 through exit tube 34. An oxygen-containing gas 36 is delivered to the reduction zone 38 via reactor shell inlet port 40. Reacted gas 42 exits the reduction zone 38 via outlet port 44.

In practice, an oxygen-containing gas or gas mixture, such as air, is passed in contact with the solid membrane in the reduction zone 6, and the reactant, hydrogen-containing gas or mixtures containing these gases is passed in contact with the solid membrane 8 in the oxidation zone 4. As the hydrogen-containing gas contacts the solid membrane, hydrogen is transferred from the hydrogen-containing gas to the surface where it is oxidized to protons and releases electrons, both of which are transported through the membrane to the surface facing the reduction zone. At the reduction zone, the protons and electrons react with the oxygen containing gas or gas mixture, producing water.

As discussed earlier, all materials to be used in membrane reactors for the above-cited reactions must meet three requirements. First, they must be conductors of protons. Second, they must conduct electrons. Third, they must be chemically and mechanically stable at the temperatures of operation and under the conditions of operation.

The materials included in this invention are inherently proton conductors or become proton conductors after a pretreatment. One pretreatment which can be given to the materials in this invention is exposure to humidified gases (hydrogen, oxygen, air or inert gas such as argon or nitrogen) in the temperature range 300° C. to 1200° C. for a period of up to one week. This pretreatment insures the initial presence of protons in the material.

Current evidence suggests that proton conduction in these materials proceeds mainly by hopping of the proton from $O^{2-}$ site to $O^{2-}$ site within the lattice. Association of the proton with an $O^{2-}$ site within the lattice results in the transient formation of $OH^-$ species. This mechanism of proton transport is to be distinguished from membranes which permit $H_2$ diffusion either directly as in Pd or through a microporous membrane. Proton transport through a solid state lattice requires a population of oxygen vacancies to be created which can subsequently accommodate oxygen anions and protons within the lattice. Depending upon the operating temperature, some perovskite lattices, e.g., $BaCeO_3$, have been shown experimentally by Bonanos, et al. (N. Bonanos, B. Ellis and M. N. Mahmood, Solid State Tonics, 28–30, 579 (1988); N. Bonanos, B. Ellis and M. N. Mahmood, Solid State Tonics, 44, 305 (1991)) capable of both proton and oxygen anion conductivity. However, at the operating temperature anticipated for the reactions of interest in this invention, proton conduction is expected to dominate. This does not preclude the use of these materials at higher temperatures where some oxygen anion conductivity will occur.

Methane oligomerization to ethylene is a specific example of the type of reaction mediated by the solid state proton and electron conducting membranes of the current invention. Methane activation in this process relies upon $O^-$ species being initially and continuously generated at an appropriately selective catalyst site in the oxidizing surface of the membrane or optional catalyst. Hydrogen abstraction from methane to give methane radicals proceeds via the general reaction:

$$M^+O^-+CH_4 \rightarrow M^+OH^-+CH_3\cdot$$

$M^+$ corresponds to an immobilized cation lattice site within the membrane or optional catalyst surface and $O^-$ to an oxidized $O^{2-}$ species. Methyl radicals formed in this manner can then dimerize in the gas phase via:

$$2CH_3\cdot \rightarrow C_2H_6$$

to give ethane. The presence of surface $O^{31}$ species have been directly observed in electron spin resonance studies on various metal oxide surfaces in heterogeneous methane oxidative dimerization reactions using $CH_4/O_2$ mixtures. Support for these methane activating species also comes from reaction between methane and metal peroxides which are the dimeric analogs of $O^-$.

Once the methane has dimerized to form ethane, ethylene would be formed by either gas phase dehydrogenation from the ethane (exothermic reaction at 750° C.) or via a surface route involving oxygen anion lattice sites on the membrane or optional catalyst surface as shown in the following scheme:

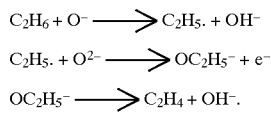

The efficiency of ethane dehydrogenation to ethylene by the latter route would, in part, be influenced by the ability of the solid state proton and electron conducting membrane to facilitate ionic transport of protons from the reaction site.

Figure 3:
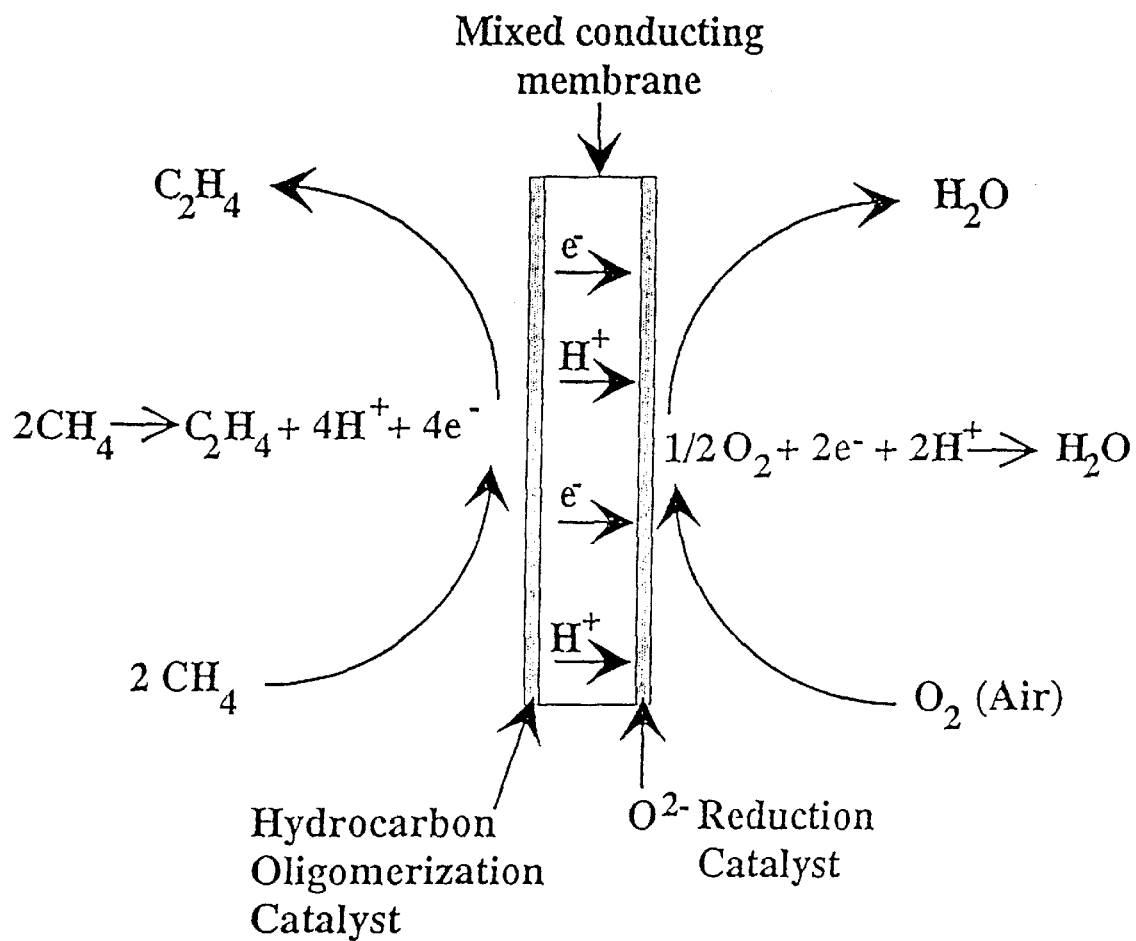
FIG. 3 is a schematic diagram of a membrane and catalysts for a process of methane conversion to ethylene.

In one process embodied by the invention, one side of the catalytic membrane reactor will be exposed to a reactant, hydrogen-containing gas or mixtures containing these gases, which are capable of being oligomerized with loss of hydrogen. These gases include methane and higher hydrocarbons. Specific examples of higher hydrocarbons include linear hydrocarbons such as ethane, propane, and butane; cyclic hydrocarbons such as cyclopropane, cyclobutane, and cyclopentane; branched hydrocarbons such as isobutane, methylpentane; and unsaturated hydrocarbons such as ethylene, propylene, and butylene. For example, in one process for which the reactor is suitable as depicted in FIG. 3, the reactant, hydrogen-containing gas is methane or natural gas, and the oxygen-containing gas or gas mixture is air. As methane or natural gas contacts the membrane, hydrogen atoms are transferred from this gas to the membrane [or the optional catalyst] surface leaving methane radicals. The methane radicals combine to form ethane and ethylene . The hydrogen atoms are oxidized to form protons and electrons, both of which are transported across the membrane and react with oxygen in the air to form $H_2O$.

Figure 4:
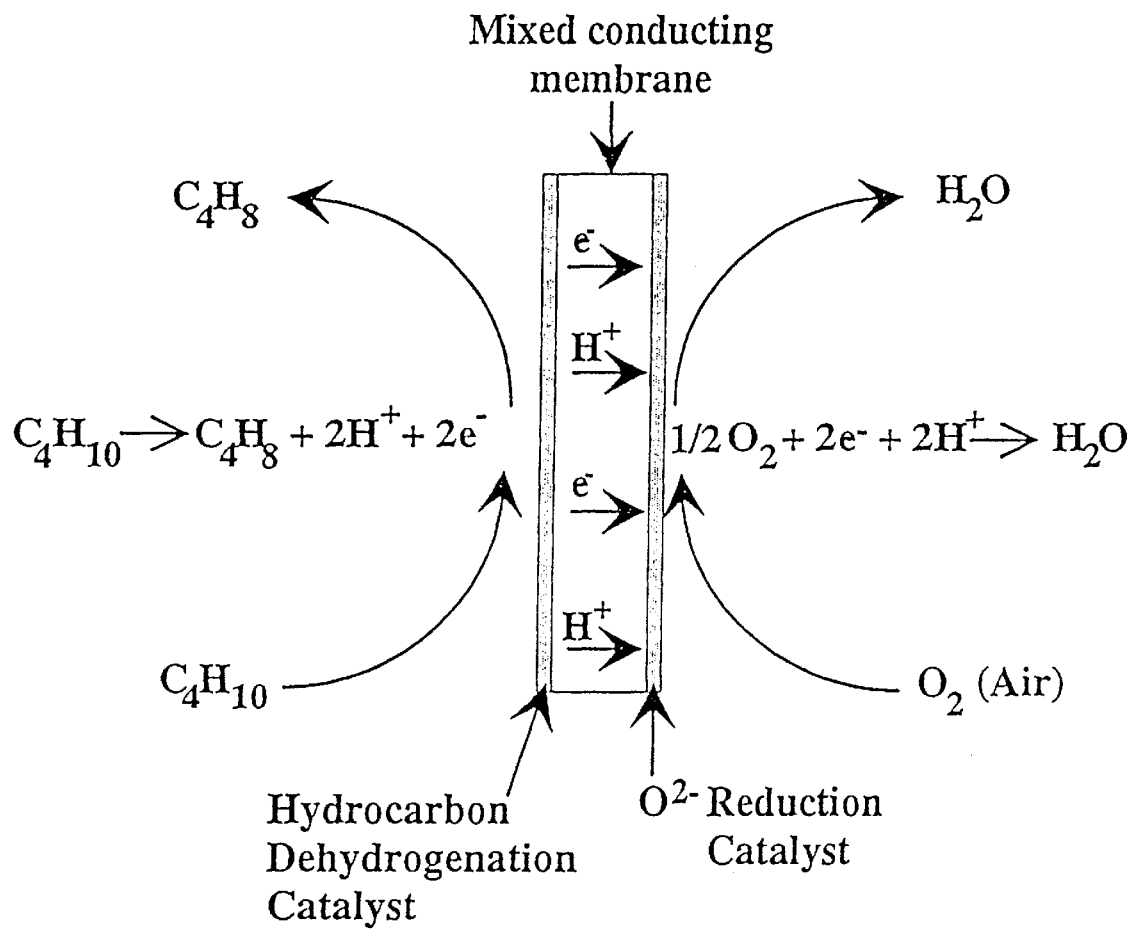
FIG. 4 is a schematic diagram of a membrane and catalysts for a process of dehydrogenation of butane to butene.
Figure 5:
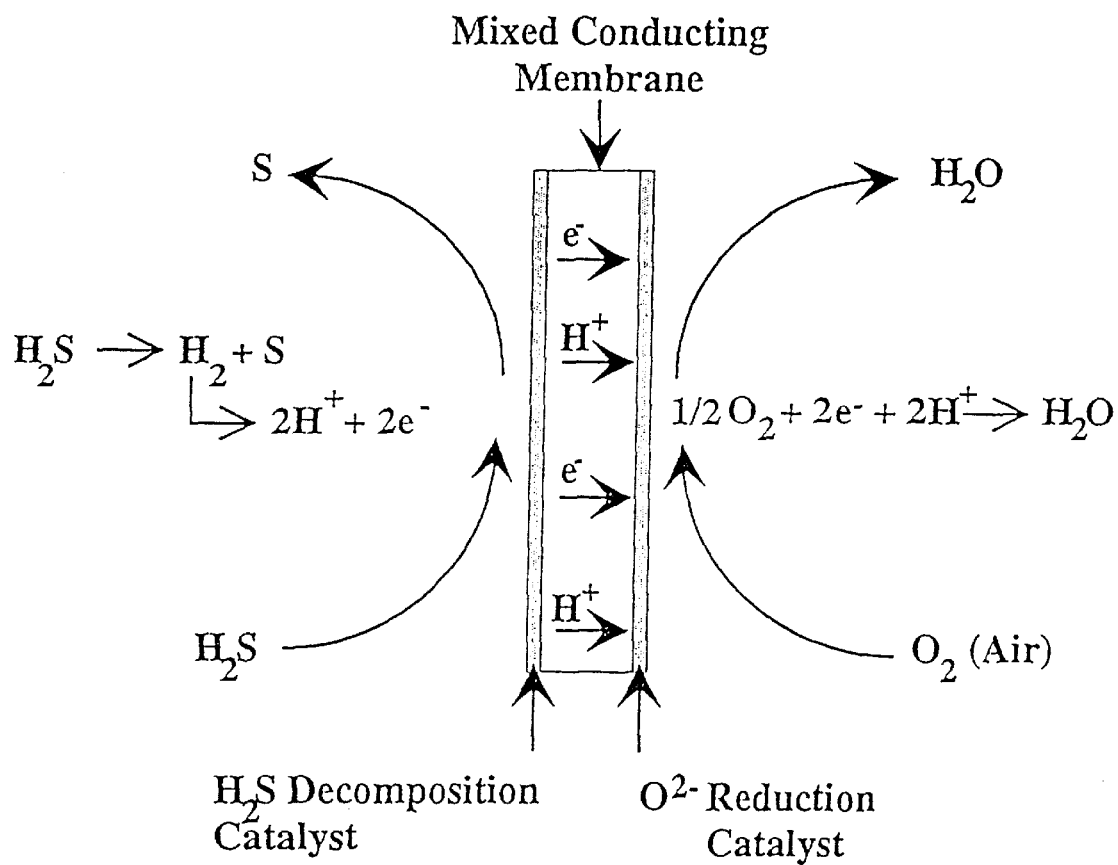
FIG. 5 is a schematic diagram of a membrane and catalysts for a process of hydrogen sulfide decomposition.
Figure 6:
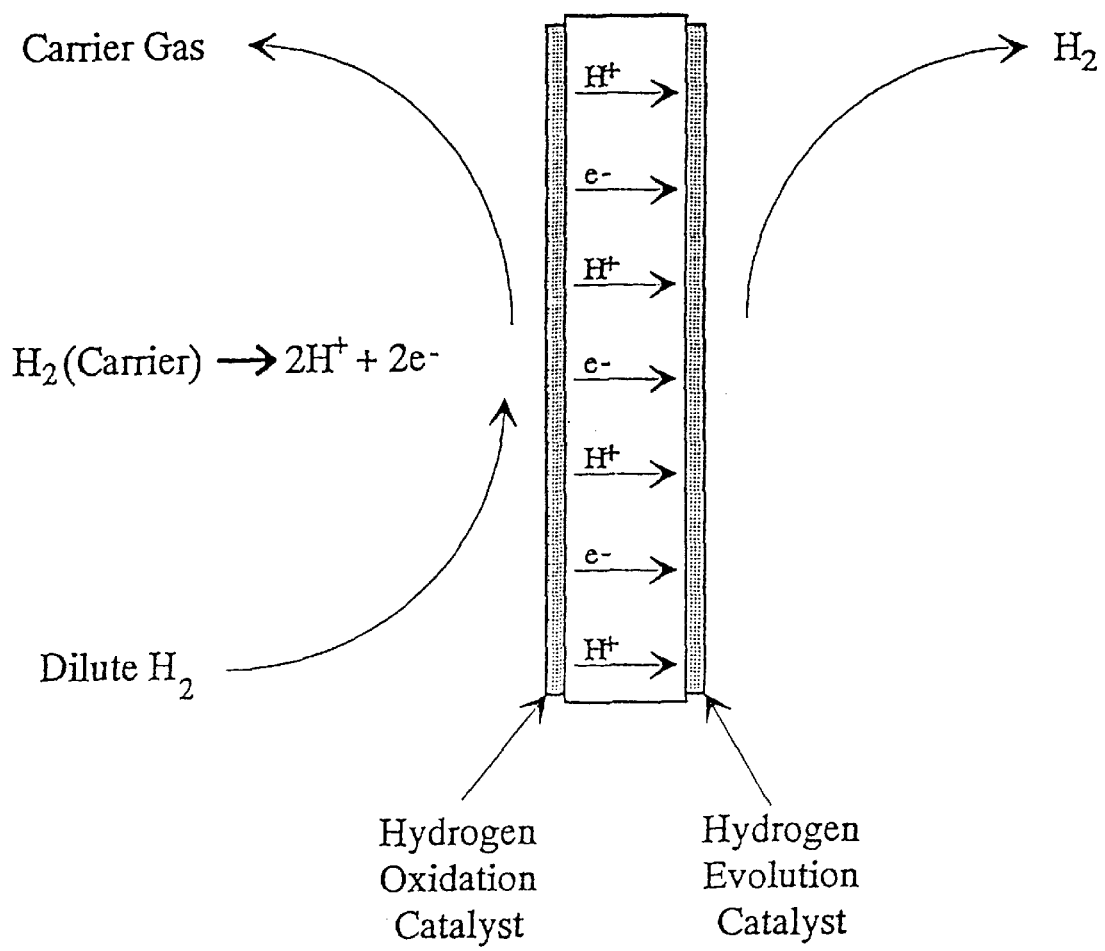
FIG. 6 is a schematic diagram of a membrane and catalysts for a process of hydrogen separation.

In a second process suitable for the catalytic membrane reactor of this invention, as depicted in FIG. 4 one side of the reactor will be exposed to a reactant, hydrogen-containing gas or mixtures containing these gases, such as those listed above. The second side is exposed to an oxygen-containing gas or gas mixture. An example is where the reactant, hydrogen-containing gas is propane and the oxygen-containing gas is air. As the propane contacts the membrane or optional catalyst surface, the propane loses hydrogen to the surface to form propene. The hydrogen is oxidized to form protons and electrons, both of which are transported across the membrane and react with oxygen in the air to form $H_2O$.

In a third process suitable for the catalytic membrane reactor of this invention, the reactant, hydrogen-containing gas is $H_2S$. One side of the reactor is exposed to this gas and the second side is exposed to an oxygen-containing gas or gas mixture, inert gas or partial vacuum in the range $10^{-1}$ to $10^{-6}$ Torr. The $H_2S$ decomposes on the membrane or optional catalyst surface to produce S and hydrogen. The hydrogen is oxidized to form protons and electrons, both of which are transported across the membrane and react with the oxygen-containing gas or gas mixture to form $H_2O$ or the inert gas or partial vacuum to form $H_2$.

Other combinations of materials reactive with each other to produce a wide range of products are possible and are contemplated as being within the scope of the present invention.

The terms "reactant, hydrogen-containing gas" and "oxygen-containing gas" herein includes materials which are not gas at temperatures below the lower temperature range, about 300° C., of the pertinent process of the present invention, and may include materials which are liquid or solid at room temperature. An example of a reactant, hydrogen-containing gas which is liquid at room temperature is pentane.

The membrane materials of the present invention have the advantage that they are mixed proton and electron conductors. The first property ensures high selectivity for the desired products of the specific reactions. Because only protons are transported through the membrane, no secondary reactions between the hydrogen-containing gas and other species, such as oxide anions, can occur. This limits unwanted side reactions thereby increasing selectivity for the desired products. The second property simplifies incorporation of these membranes into reactors for eventual application. The simplification in reactor design arises due to the fact that electrodes and an external electrical circuit for transporting the electrons generated at the oxidating surface to the reducing surface are not necessary as the electron-conducting membrane serves as the circuit itself. These two properties distinguish the membrane materials of the current invention from those previously known.

Preferred materials to be used in the solid state proton and electron mediating membranes of this invention are formed from perovskite compounds of general stoichiometry $AB_{1-x}B'_xO_{3-y}$, where A=Ca, Sr or Ba; B=Ce, Tb, Pr or Th; B'=Ti, V, Cr, Mn, Fe, Co, Ni, Cu, Al, Ga or, In or combinations thereof; and $0.02<x<0.5$.

In addition to the solid state proton and electron mediating membrane discussed above, optional catalysts may also be used on the membrane surfaces. The purpose of the catalyst is to promote one specific reaction over another. Similarly, the catalyst can enhance the rate of a particular reaction. The specific catalysts will depend on the specific reaction for which the catalytic membrane reactor is to be used. However, the catalysts in general must meet certain requirements. As the reactions involve hydrogen abstraction, basicity is an important property. Additionally, the catalysts need to have a certain degree of both electron and proton conductivity as both of these species need to be transported to the membrane.

For hydrocarbon oligomerization and dehydrogenation reactions, preferred catalysts include the oxides of the first row transition metals supported on the alkali metal oxides, the metals Ni, Fe, Pt, Ag or Pd and their alloys, and perovskite compounds $AB_{1-x}B'_xO_{3-y}$ where A=Ca, Sr or Ba; B=Ce, Tb, Pr or Th; and B'=Ti, V, Cr, Mn, Fe, Co, Ni or Cu; and $0.02<x<0.5$.

For the process of $H_2S$ decomposition, an additional desirable property of the catalyst is sulfur tolerance, i.e., the catalyst must not react with sulfur so that the activity of the catalyst is impaired. In $H_2S$ decomposition, the preferred catalysts are thiospinels $AB_2S_4$ (where A is a $2^+$ group VIII ion and B is a $3^+$ Group VIII ion) or $WS_2$.

For all the above applications, a catalyst may be advantageously used on the reducing side of the membrane in contact with oxygen or an oxygen-containing gas. For the reduction of oxygen, the preferred catalysts are Ag, $La_{1-x}Sr_xCOO_{3-y}$ where $0.2 \leq x \leq 0.5$, and $ACo_{1-x}M_xO_{3-y}$ where A=Ca, Sr and Ba, and M=Fe, Co, and Ni where $0 \leq x \leq 0.5$.

In one example of the present invention, a catalytic membrane reactor with the material $BaCe_{0.9}Mn_{0.1}O_{3-y}$ serving as the membrane was fabricated. The material was fabricated into a membrane by initially preparing powders using standard solid state synthetic techniques. This involved repeatedly calcining and milling powders of the individual metal oxides or carbonates in the desired stoichiometric ratio. These powders were then repeatedly calcined at temperatures up to 1400° C. for 12-hour time periods. In between calcinations, the powders were milled thoroughly. This procedure was continued until a single phase material was obtained. The resulting powders were pressed and sintered at 1500° C. for four hours to obtain a sintered disk of $\geq 90\%$ theoretical density. It must be noted that the specific experimental details for the preparation of the membranes will be dependent on the specific material. In particular, the optimal temperature for membrane preparation will vary from about 1300° C. to 1700° C.

The sintered membrane was incorporated into a two-zone reactor with a pyrex seal used to isolate the two zones. A generic reactor is illustrated in FIG. 1. While FIG. 1 utilizes a cylindrical-shaped membrane, the principles of operation are the same as for a disk-shaped membrane, and are not dependent upon the shape of the membrane. No catalysts were used in this specific example. One side of the reactor was exposed to oxygen and the second side to methane. The reactor was heated to 950° C. and the product stream from the methane side of the reactor was analyzed by gas chromatography. The results indicated rates of methane to ethylene oligomerization of $75 mA/cm^2$ with a 1 mm thick membrane. This translates into a rate for ethylene production of 0.2 ml(STP) $min^{-1}$ $cm^{-2}$. The selectivity for ethylene was close to 100%, with the other products being acetylene and ethane. No decomposition or instability of the membrane was observed after one week of operation.

In another example of the present invention a catalytic membrane reactor with the material $SrCe_{0.98}Fe_{0.02}O_{3-y}$ serving as the membrane was fabricated in a manner similar to that described above. On one surface of the sintered membrane, the catalyst $WS_2$, obtained commercially, was applied. On the second side of the membrane, an Ag catalyst was applied using commercially available Ag epoxy. The catalyst-coated membrane was incorporated into a two-zone reactor.

Once the reactor had reached an operating temperature of 850° C., a flow of $H_2S$ was admitted to the oxidation zone (in which the $WS_2$-coated side of the membrane was exposed) and an $O_2$ stream was admitted to the Ag-coated (reduction) side of the membrane. The $H_2S$ was decomposed to yield S in the oxidation zone, and to yield $H_2O$ in the reduction zone. The rate in electrochemical terms was $11 mA/cm^2$ for a 2 mm thick membrane. This rate corresponds to a $H_2S$ decomposition rate of 0.1 ml(STP) $min^{-1}$ $cm^{-2}$. It was observed that the degree of $H_2S$ decomposition using the membrane reactor was 129% of that expected for the simple thermal decomposition reaction of $H_2S$ under equilibrium conditions at this temperature. This result demonstrates the effectiveness of the membrane to create non-equilibrium conditions, and therefore enhance the decomposition reaction, through the active transport of hydrogen, as protons, away from the reaction zone. No decomposition or instability of either the membrane or catalyst were observed after one week of operation.

In another example of the present invention, a reactor was fabricated similar to that above except the solid state proton and electron mediating membrane was $SrCe_{0.9}Fe_{0.1}O_{3-y}$ and Ar was used in place of oxygen in the reduction zone. At the operating temperature of 825° C., the $H_2S$ decomposed to yield S in the oxidation zone and $H_2$ in the reduction zone. $H_2$ removal rates were up to 100% of that expected from the measured proton conductivity of the membrane. No decomposition or instability of either the membrane or catalyst were observed after one week of operation.

We claim:

1. A catalytic membrane which is a proton and electron mediating membrane for reacting a hydrogen-containing gas with an oxygen-containing gas, an inert gas or a partial vacuum in an oxidation-reduction reaction, said membrane having a reduction surface and an oxidization surface and said membrane comprising a single-phase mixed metal oxide material of formula:

$$AB_{1-x}B'_xO_{3-y}$$

wherein A is selected from Ca, Sr or Ba ions; B is selected from Ce, Tb, Pr, or Th ions; B' is selected from Ti, V, Cr, Mn, Fe, Co, Ni, Cu, Al, Ga, or In ions, or combinations thereof; y depends upon the valences A, B and B' and is a number that provides for charge balancing and x is greater than or equal to 0.02 and less than or equal to 0.5.

2. The membrane of claim 1 further comprising a catalyst on said oxidation surface, said reduction surface, or both.

3. The membrane of claim 1 or 2 wherein said single-phase mixed metal oxide material is both an electron conductor and a proton conductor.

4. The membrane of claim 1 wherein A is a Sr ion, B is a Ce ion, and B' is an Fe ion.

5. The membrane of claim 4 comprising the single-phase mixed oxide material Sr Ce$_{0.98}$Fe$_{0.02}$O$_{3-y}$.

6. The membrane of claim 5 further comprising a catalyst on said oxidation surface, said reduction surface, or both.

7. The membrane of claim 6 wherein said catalyst on said oxidation surface is WS$_2$ and said catalyst on said reduction surface is Ag.

8. The membrane of claim 4 comprising the single-phase mixed oxide material Sr Ce$_{0.9}$Fe$_{0.1}$O$_{3-y}$.

9. The membrane of claim 8 further comprising a catalyst on said oxidation surface, said reduction surface, or both.

10. The membrane of claim 9 wherein said catalyst on said oxidation surface is WS$_2$ and said catalyst on said reduction surface is Ag.

11. The membrane of claim 1 wherein A is a Ba ion, B is a Ce ion, and B' is a Mn ion.

12. The membrane of claim 11 comprising the single-phase mixed metal oxide BaCe$_{0.9}$Mn$_{0.1}$O$_{3-y}$.

13. The membrane of claim 12 having a catalyst on said oxidation surface and wherein said catalyst is selected from the oxides of first row transition metals supported on an alkali metal oxide, or the metals Ni, Fe, Pt, Ag, or Pd.

14. The membrane of claim 12 having a catalyst on said oxidation surface and wherein said catalyst is a perovskite compounds of the formula: AB$_{1-x}$B'$_x$O$_{x-y}$, where A can be a Ca, Sr or Ba ion, B can be Ce, Tb, Pr, or Th and B' can be Ti, V, Cr, Mn, Fe, Co, Ni, or Cu and x is greater than or equal to 0.02 and less than or equal to 0.5.

15. The membrane of claim 12 having a catalyst on said oxidation surface and wherein said catalyst is either Ws$_2$ or a thiospinel compound of the composition AB$_2$S$_4$ where A is a 2$^+$group VIII ion and B is a 3$^+$Group VIII ion.

16. The membrane of claim 11 further comprising a catalyst on the reduction surface and wherein said catalyst is selected from: Ag; La$_{1-cx}$Sr$_x$CoO$_{3-y}$, where x is greater than or equal to 0.2 and less than or equal to 0.5; or ACo$_{1-x}$M$_x$O$_{3-y}$, where A can be a Ca, Sr, or Ba ion, M can be an Fe, Co, or Ni ion and x is greater than or equal to 0 and less than or equal to 0.5.

17. The membrane of claim 11 having a catalyst on the reduction surface and wherein said catalyst is selected from: Ag; La$_{1-x}$Sr$_x$CoO$_{3-y}$, where x is greater than or equal to 0.2 and less than or equal to 0.5; or ACo$_{1-x}$M$_x$O$_{3-y}$, where A can be a Ca, Sr, or Ba ion, M can be an Fe, Co, or Ni ion and x is greater than or equal to 0 and less than or equal to 0.5.

18. A catalytic membrane which is a proton and electron mediating membrane fabricated by (a) combining powders of metal oxides or metal carbonates of metal ion A, metal ion B and metal ion B' such that the stoichiometric ratio A:B:B' is 1:1-x:x where $0.2 \leq x \leq 0.5$, A is selected from Ca, Sr or Ba; B is selected from Ce, Tb, Pr or Th; and B' is selected from T, V, Cr, Mn, Fe, Co, Ni, Cu, Al, Ga, or In;

(b) repeatedly calcining and milling said combined powders until a single phase material is obtained, and (c) pressing and sintering said single phase material to obtain a membrane.

19. The membrane of claim 18 wherein metal ion B' is Al, Ga or In.

20. The membrane of claim 18 wherein metal ion A is Sr and B is Ce.

21. The membrane of claim 20 wherein metal ion B' is Fe.

22. The membrane of claim 18 wherein metal ion A is Ba and B is Ce.

23. The membrane of claim 22 wherein metal ion B' is Mn.

* * * * *

UNITED STATES PATENT AND TRADEMARK OFFICE
CERTIFICATE OF CORRECTION

PATENT NO. : 5,821,185

DATED : Oct. 13, 1998

INVENTOR(S) : White et al.

It is certified that error appears in the above-identified patent and that said Letters Patent is hereby corrected as shown below:

On the title page, Item [57] Abstract,

At the 7$^{th}$ line from the bottom, please rewrite "fabricated-by" as --fabricated by--.

At the 4$^{th}$ line from the bottom, please rewrite "0.2≤x0.5," as --$0.2 \leq x \leq 0.5$,--.

Signed and Sealed this

Eleventh Day of May, 1999

Attest:

Q. TODD DICKINSON

*Attesting Officer*   *Acting Commissioner of Patents and Trademarks*